United States Patent
Will et al.

(10) Patent No.: US 8,652,775 B2
(45) Date of Patent: Feb. 18, 2014

(54) ALKYL AMINES IMPROVE DETECTION OF COMPONENTS OF FORMALDEHYDE-FIXED BIOLOGICAL SAMPLES

(75) Inventors: Stephen G. Will, Oakland, CA (US); Veeraiah Bodepudi, San Ramon, CA (US); Ellen H. Fiss, Albany, CA (US); Rachel Shahinian, Alameda, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 503 days.

(21) Appl. No.: 12/079,694

(22) Filed: Mar. 28, 2008

(65) Prior Publication Data

US 2009/0081661 A1    Mar. 26, 2009

Related U.S. Application Data

(60) Provisional application No. 60/954,721, filed on Aug. 8, 2007, provisional application No. 60/920,939, filed on Mar. 30, 2007.

(51) Int. Cl.
*C12Q 1/68* (2006.01)
(52) U.S. Cl.
USPC .......................................... 435/6.1; 435/6.11
(58) Field of Classification Search
None
See application file for complete search history.

(56) References Cited

U.S. PATENT DOCUMENTS

| | | | |
|---|---|---|---|
| 6,649,368 B1 | 11/2003 | Aghassi et al. | |
| 7,318,925 B2 * | 1/2008 | Roskos et al. | ............. 424/145.1 |
| 2004/0029184 A1 | 2/2004 | Gourevitch | |
| 2010/0056769 A1 | 3/2010 | Ritt et al. | |

FOREIGN PATENT DOCUMENTS

| | | |
|---|---|---|
| EP | 2008002356 | 7/2008 |
| WO | 9404906 A1 | 3/1994 |
| WO | 2006066039 A2 | 6/2006 |
| WO | 2006066039 A3 | 6/2006 |
| WO | WO-2006/066039 | 6/2006 |
| WO | WO 2007/068764 A1 | 6/2007 |

OTHER PUBLICATIONS

Cao et al., "Expression of MDR1 mRNA and Encoding P-glycoprotein in Archival Formalin-fixed Paraffin-embedded Gall Bladder Cancer Tissues." European Journal of Cancer, vol. 34, No. 10, pp. 1612-1617.*
Olmedilla et al., "Visualization of starch-synthase expression by in situ hybridization during pollen development," Planta, 1991, vol. 184, pp. 182-186.*
Shi, Shan-Rong, et al., 1999, "Standardization and Further Development of Antigen Retrieval Immunohistochemistry: Strategies and Future Goals," The Journal of Histotechnology, 22(3):177-192.
Namimatsu, Shigeki et al.; "Reversing the Effects of Formalin Fixation with Citraconic Anhydride and Heat: A Universal Antigen Retrieval Method"; 2005, *The Journal of Histochemistry & Cytochemistry*, vol. 51, No. 1, pp. 3-11.
Shan-Rong Shi et al.; "Antigen Retrieval Technique Utilizing Citrate Buffer or Urea Solution for Immunohistochemical Demonstration of Androgen Receptor in Formalin-fixed Paraffin Sections"; 1993, *The Journal of Histochemistry & Cytochemistry*, vol. 41, No. 11, pp. 1599-1604.
Shan-Rong Shi et al.; "Antigen Retrieval Immunohistochemistry: Past, Present, and Future"; *The Journal of Histochemistry & Cytochemistry*, vol. 45, No. 3, pp. 327-343.
Shan-Rong Shi et al.; "DNA extraction from archival formalin-fixed, paraffin-embedded tissues: heat-induced retrieval in alkaline solution"; 2004, *Histochem Cell Biol.*, vol. 122, pp. 211-218.
Shi, Shan-Ring et al.; "DNA Extraction from Archival Formalin-fixed, Paraffin-embedded Tissue Sections Based on the Antigen Retrieval Principle: Heating Under the Influence on pH"; 2002, *The Journal of Histochemistry & Cytochemistry*, vol. 50, No. 8, pp. 1005-1011.
Shi, Shan-Ring et al.; "DNA Extraction from Archival Formalin-fixed, Paraffin-embedded tissues: heat-induced retrieval in alkaline solution"; 2004, *Histochem Cell Blood*, vol. 122, pp. 211-218.
Wu, Lin et al.; "Extraction and Amplification of DNA From Formalin-Fixed, Paraffin-Embedded Tissues"; 2002, *Applied Immunohistochemistry & Molecular Morphology*, vol. 10, No. 3, pp. 269-274.

* cited by examiner

*Primary Examiner* — Young J Kim
(74) *Attorney, Agent, or Firm* — Kilpatrick Townsend & Stockton LLP

(57) ABSTRACT

Alkyl amines act to release formaldehyde cross-linking that occurs in biological samples. Thus, contacting alkyl amines to formaldehyde fixed samples is a useful way to render biological components of the samples, including nucleic acids or proteins, more accessible to detection and characterization.

5 Claims, 15 Drawing Sheets

Cross-Linking Chemistry

FFPET sample: Reversal of Cross-link with EDA

Treatment of FFPET samples with increasing amount of EDA in sample prep

Line 1: Marker
Line 2 and 3: BSA
Line 4: BSA+Formalin, 14 hours
Line 5: BSA+Formalin (14 hours)+EDA
Line 6: BSA+Formalin (36 hours)+EDA
Line 7: BSA+Formalin (36 hours)+EDA
Line 8: BSA+Formalin (36 hours)+EDA

ALKYL AMINES IMPROVE DETECTION OF COMPONENTS OF FORMALDEHYDE-FIXED BIOLOGICAL SAMPLES

CROSS-REFERENCE TO RELATED PATENT APPLICATIONS

The present application claims benefit of priority to U.S. Provisional Patent Application No. 60/920,939, filed Mar. 30, 2007, and U.S. Provisional Patent Application No. 60/954,721, filed Aug. 8, 2007, each of which is incorporated by reference in their entirety.

BACKGROUND OF THE INVENTION

For over a hundred years, pathologists have routinely preserved biological samples such as tissue samples by fixing them with formaldehyde. While formaldehyde treatment preserves the cellular features of the tissue, formaldehyde treatment also results in chemical cross-linking that renders many of the biological components of the sample poorly accessible or inaccessible to detection, quantification and characterization. Formaldehyde preserves or fixes tissue or cells by cross-linking primary amine groups in proteins with other nearby nitrogen atoms in protein or DNA through a —CH2— linkage. Thus, for example, while the polymerase chain reaction (PCR) is useful to detect and quantify nucleic acids in biological samples, PCR is generally poorly or not effective in analyzing nucleic acids in formaldehyde cross-linked samples, especially where quantitative results are desired.

Cross-linking of nucleic acids to cellular components by the action of formaldehyde thus presents challenges to the detection of various cellular components, including detection of nucleic acids and proteins. While some have described ways of improving amplification of nucleic acids from formaldehyde cross-linked samples, the improvements generally involve merely degrading protein in the sample or providing detergents that do not generally change the covalent bonds forming the cross-links. The present invention addresses this and other problems.

BRIEF SUMMARY OF THE INVENTION

The present invention provides methods for analyzing one or more components of a formaldehyde cross-linked biological sample. In some embodiments, the methods comprise contacting the sample with a sufficient amount of an alkyl amine to release at least a portion of the cross-linked component, thereby improving the accessibility of the one or more components for analysis.

In some embodiments the biological sample is a tissue sample from an animal.

In some embodiments the amount of alkyl amine is between 0.01% (about 2 mM) and 5% (about 800 mM).

In some embodiments the sample and alkyl amine are heated for a period of time.

In some embodiments, the methods further comprise detecting the component.

In some embodiments, the alkyl amine is substantially removed from the sample prior to the detecting step. In some embodiments, the concentration of alkyl amine is reduced to less than about 0.5% (about 80 mM) (e.g., less than about 0.2% or 0.1%) prior to the detecting step.

In some embodiments, the detecting step comprises quantifying the component.

In some embodiments, the component is a nucleic acid. In some embodiments, the nucleic acid is DNA. In some embodiments, the component is RNA.

In some embodiments, the methods further comprise detecting the nucleic acid. In some embodiments, the detecting step comprises amplifying the nucleic acid. In some embodiments, the nucleic acid component is contacted to a probe under conditions to allow for formation of the probe and nucleic acid, and detecting the presence of the duplex. In some embodiments, the probe is linked to a solid support. In some embodiments, the amplifying step comprises the polymerase chain reaction.

In some embodiments, the component is protein. In some embodiments, the methods further comprise detecting the protein. In some embodiments, the detecting step comprises mass spectrometry or electrophoresis. In some embodiments, the mass spectrometry comprises matrix-assisted laser desorption/ionization (MALDI).

In some embodiments, the sample is embedded in paraffin prior to the contacting step.

In some embodiments, the alkyl amine is selected from the group consisting of ethylenediamine, ethanolamine, and propylamine.

In some embodiments, the portion of the component that is available for analysis is increased at least about two-fold compared to the portion accessible for analysis if the contacting step is not performed. In some embodiments, the portion of the component that is available for analysis is increased at least about ten-fold compared to the portion accessible for analysis if the contacting step is not performed.

In some embodiments, the methods further comprise contacting the sample with a protease to degrade the protein in the sample, thereby rendering the nucleic acids more available for analysis.

The present invention also provides a kit for improving the availability of one or more components of a formaldehyde cross-linked biological sample. In some embodiments, the kit comprises an alkyl amine; and a protease or a reagent or device for removal of the alkyl amine from a biological sample.

In some embodiments, the kit comprises a reagent or device for removal of the alkyl amine from a biological sample. In some embodiments, the device is a column for purification of nucleic acids.

In some embodiments, the kit comprises a protease. In some embodiments, the protease is proteinase K.

In some embodiments, the kit further comprises nucleotides and/or a thermostable polymerase. In some embodiments, the thermostable polymerase is Taq polymerase.

The present invention also provides reaction mixtures. In some embodiments, the reaction mixtures comprise a formaldehyde cross-linked biological sample; and a sufficient amount of an alkyl amine to release at least a portion of the cross-linked component.

In some embodiments, the amount of alkyl amine is between 0.01% and 5%. In some embodiments, the alkyl amine is selected from the group consisting of ethylenediamine, ethanolamine, and propylamine. In some embodiments, the biological sample is a tissue sample from an animal.

DEFINITIONS

A "formaldehyde cross-linked biological sample" refers to a biological sample that has been treated with formaldehyde such that cross-linking is formed between a nitrogen in a protein to other nitrogen-containing proteins and/or nucleic acids. A biological sample will typically contain cells. The biological sample can be, for example, a tissue sample from an animal. Many formaldehyde-treated samples are stored by embedding them in paraffin.

As used herein, the term "alkyl amine" refers to a straight or branched, saturated or unsaturated, molecule having 1-10 or more carbon atoms and one or more amino groups. The alkyl portion of the alkyl amine can be methyl, ethyl, propyl, butyl, pentyl, hexyl, iso-propyl, iso-butyl, sec-butyl, tert-butyl, etc. The amino groups can be primary or secondary. The alkyl amine can be further substituted with no more than two (i.e., 0, 1, or 2) substituents including, but not limited to, one or more hydroxy groups. Alkyl amines useful in the present invention include, but are not limited to, ethyl amine, propyl amine, isopropyl amine, ethylene diamine and ethanolamine. One of skill in the art will appreciate that other alkyl amines are useful in the present invention.

The phrase "detecting the component" refers to determining at least the presence or absence of the component and can include further quantification or other characterization of the component or part of the component.

A "component" of a biological sample refers to a class of molecules (e.g., proteins, nucleic acids, etc.) or a specific target such as a specific protein or nucleic acid sequence that one wishes to detect.

As used herein, the term "nucleic acid" refers to polymers of deoxyribonucleotides (containing 2-deoxy-D-ribose) (i.e., DNA), polyribonucleotides (containing D-ribose) (i.e., RNA), and any other N-glycoside analogs of a purine or pyrimidine base, or modified purine or pyrimidine bases.

The phrase "to release at least a portion of the cross-linked component" refers to altering the covalent bonds forming a cross-linkage between two components (e.g., a nucleic acid and a protein) of the biological sample such that the two components are no longer linked by a covalent bond. The phrase encompasses, but is not limited to, a complete reversal of the cross-linking process.

The phrase "accessibility for analysis" as used herein refers to the ability of a detection method to determine the presence or absence and/or quantity of a particular target molecule. For example, numerous detection methods are at least partly inhibited from detecting protein or nucleic acids in a formaldehyde cross-linked biological sample and thus certain cross-linked components are not "accessible" for detection. Once cross-linking is released by treatment with an alkyl amine, an increased amount (e.g., at least about 10% more and typically at least about 2-fold more, or sometimes about at least 10 or 100-fold more) of the component can be detected and quantified.

DETAILED DESCRIPTION OF THE INVENTION

I. Introduction

Figure 1:
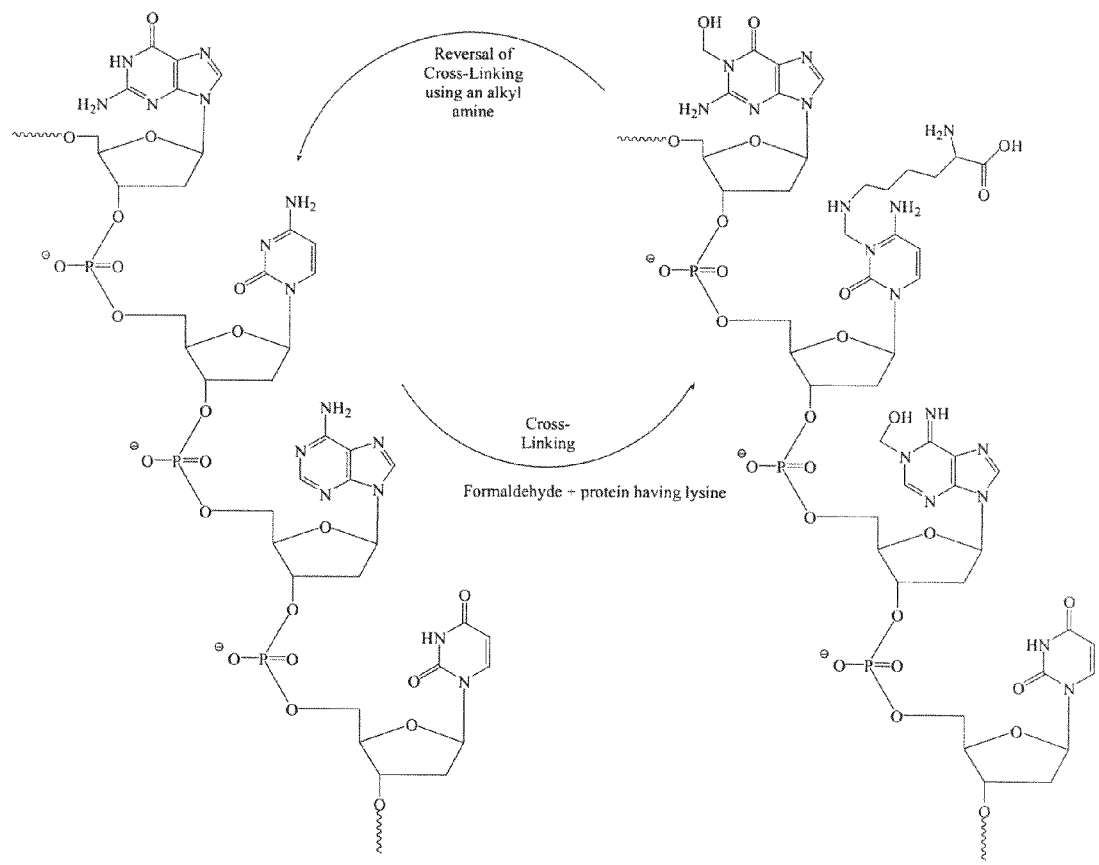
FIG. 1 illustrates an example of formaldehyde cross-linking of nucleic acids to lysine and the reversal of the cross-linking upon addition of an alkyl amine.
Figure 2:
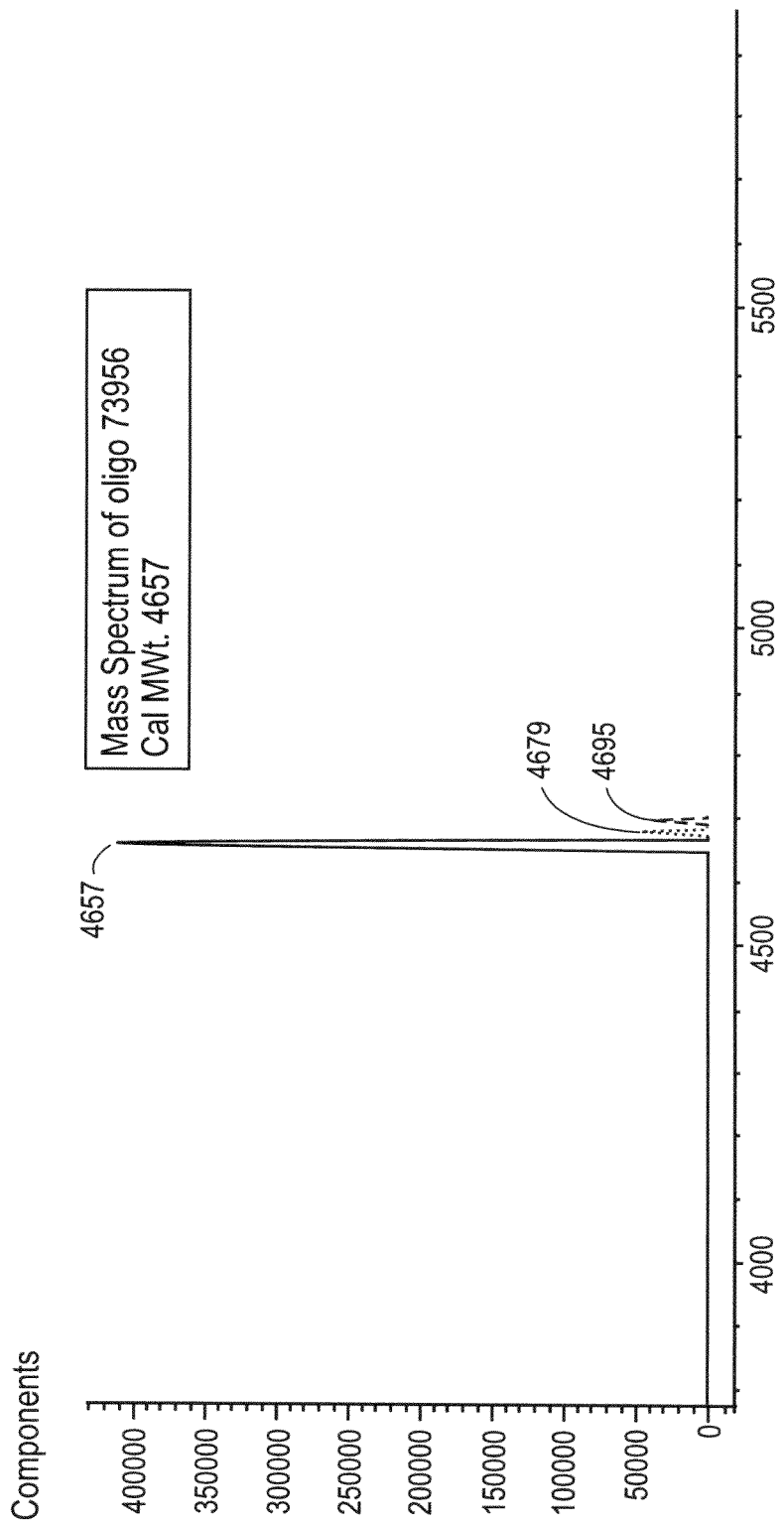
FIG. 2 illustrates mass spectrometry analysis of the untreated oligonucleotide described in Example 1.
Figure 3:
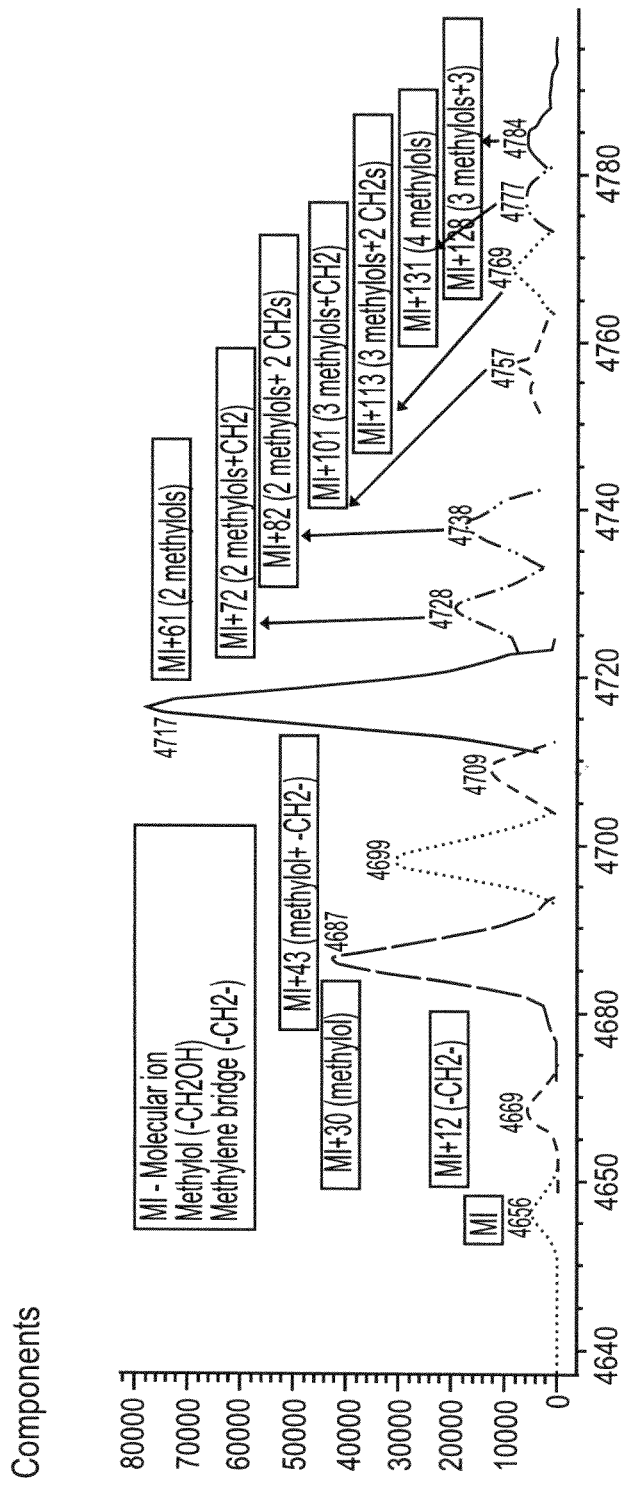
FIG. 3 illustrates mass spectrometry analysis of the formalin-treated oligonucleotide described in Example 1.
Figure 4:
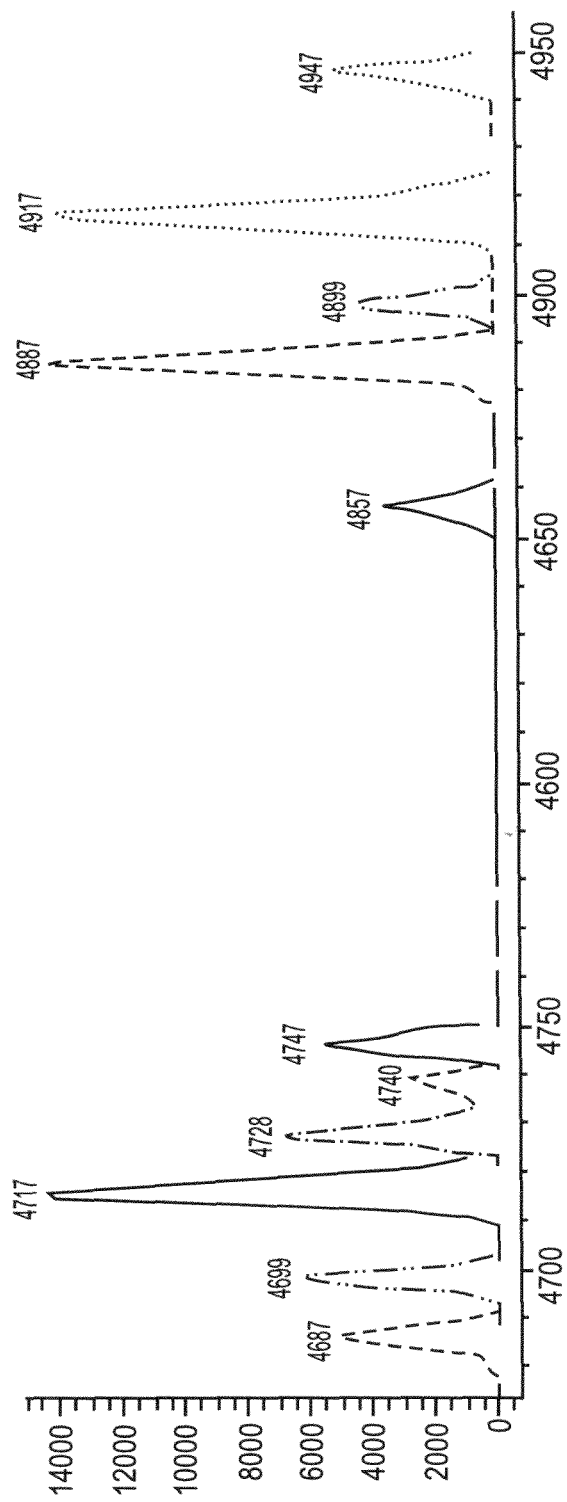
FIG. 4 illustrates mass spectrometry analysis of the formalin-treated mixture of the oligonucleotide and lysine as described in Example 1.
Figure 5:
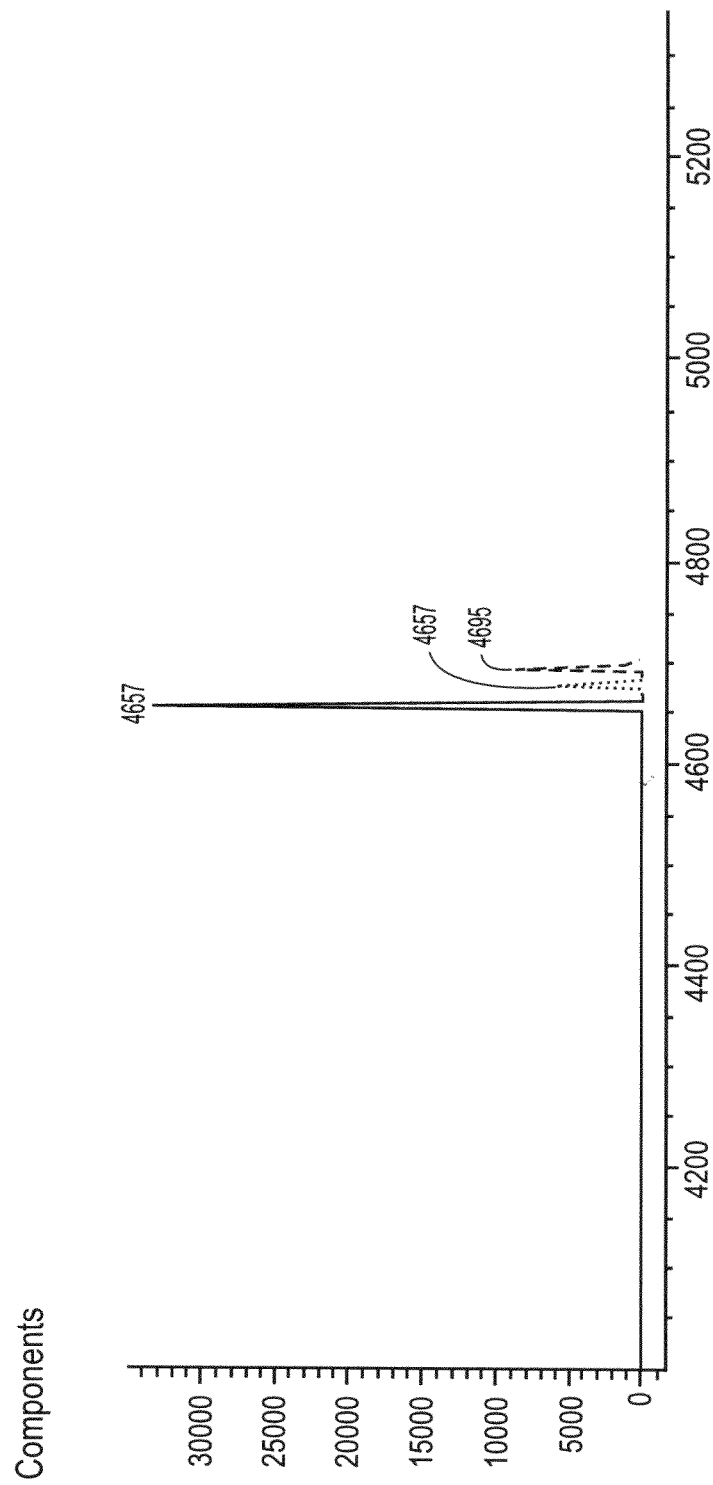
FIG. 5 illustrates mass spectrometry analysis of the formalin-treated oligonucleotide and lysine mixture following treatment with ethanoldiame thereby regenerating starting DNA from cross-linked DNA-lysine adducts as described in Example 1.
Figure 6:
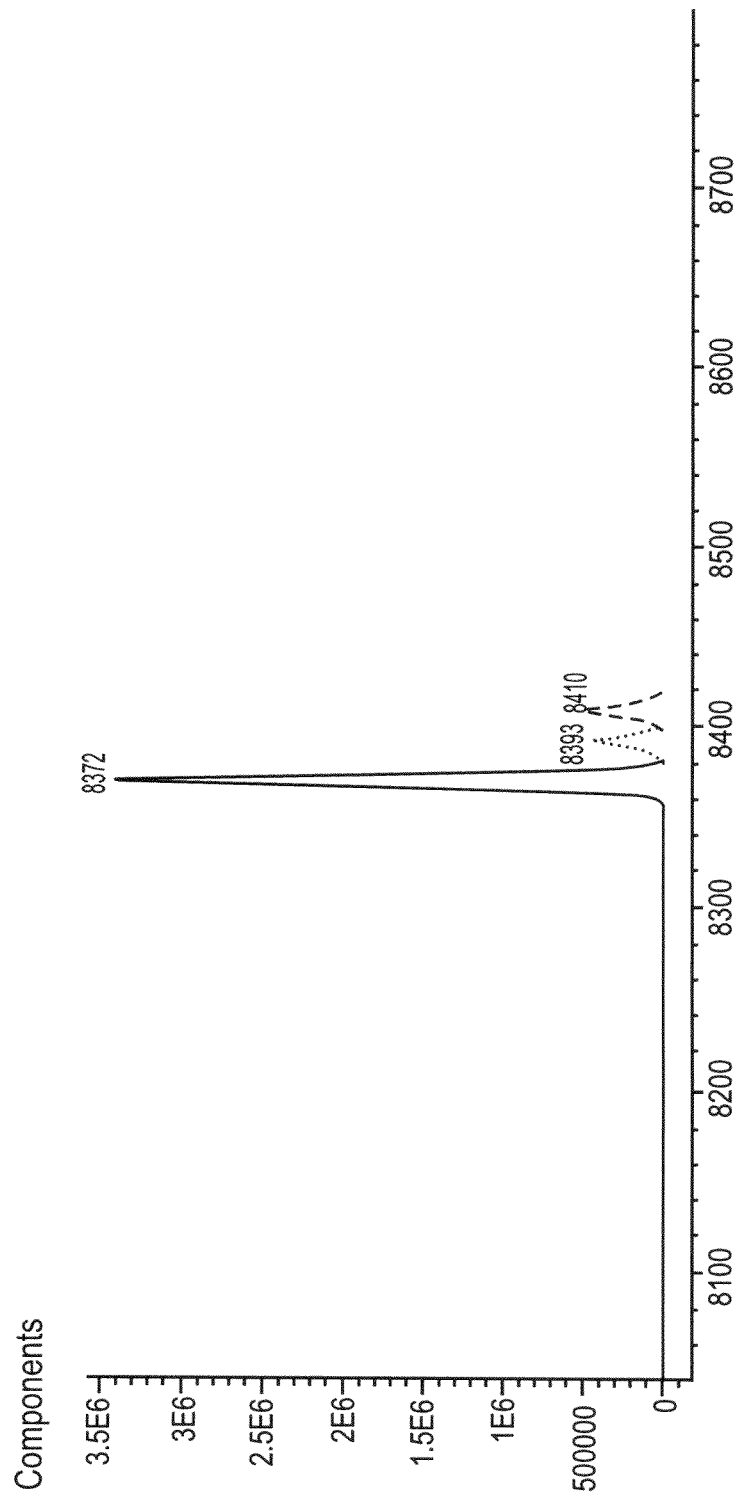
FIG. 6 illustrates mass spectrometry analysis of the untreated synthetic RNA.
Figure 7:
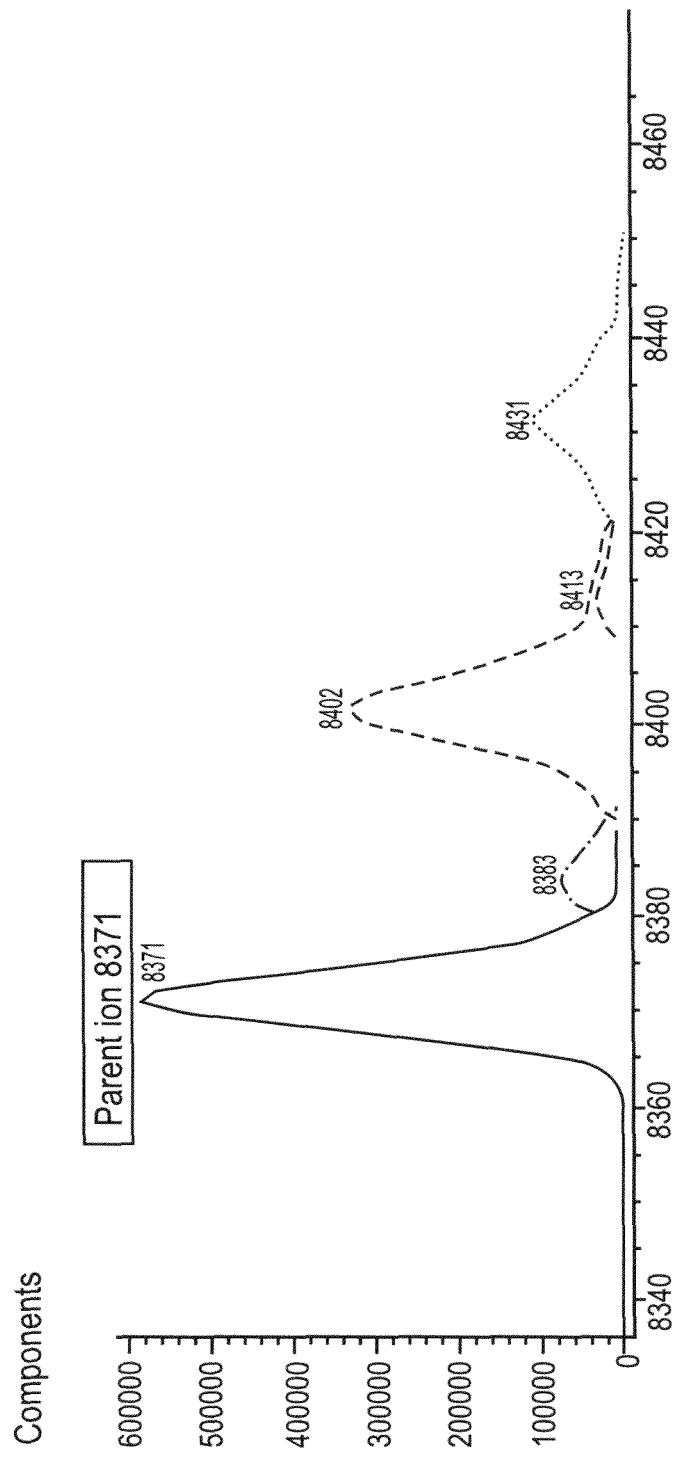
FIG. 7 illustrates mass spectrometry analysis of the synthetic RNA following a one hour incubation with formalin.
Figure 8:
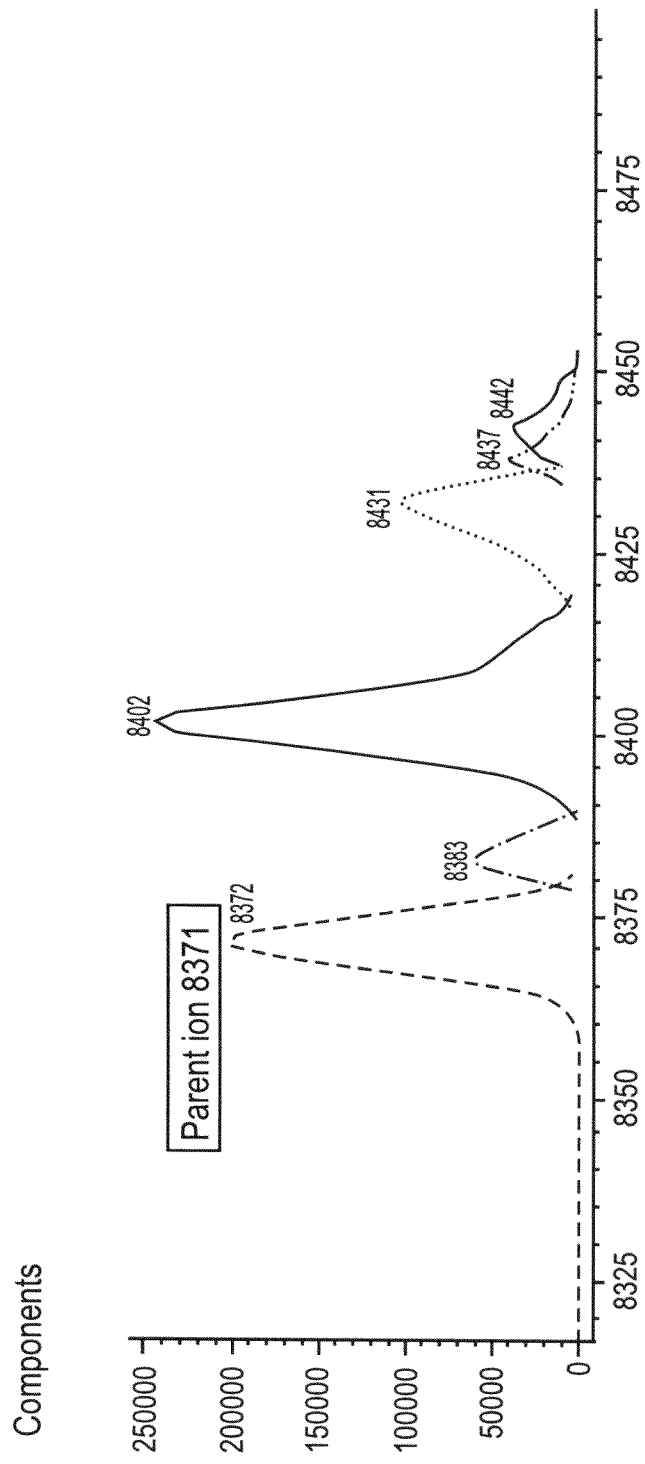
FIG. 8 illustrates mass spectrometry analysis of the synthetic RNA following a five hour incubation with formalin.
Figure 9:
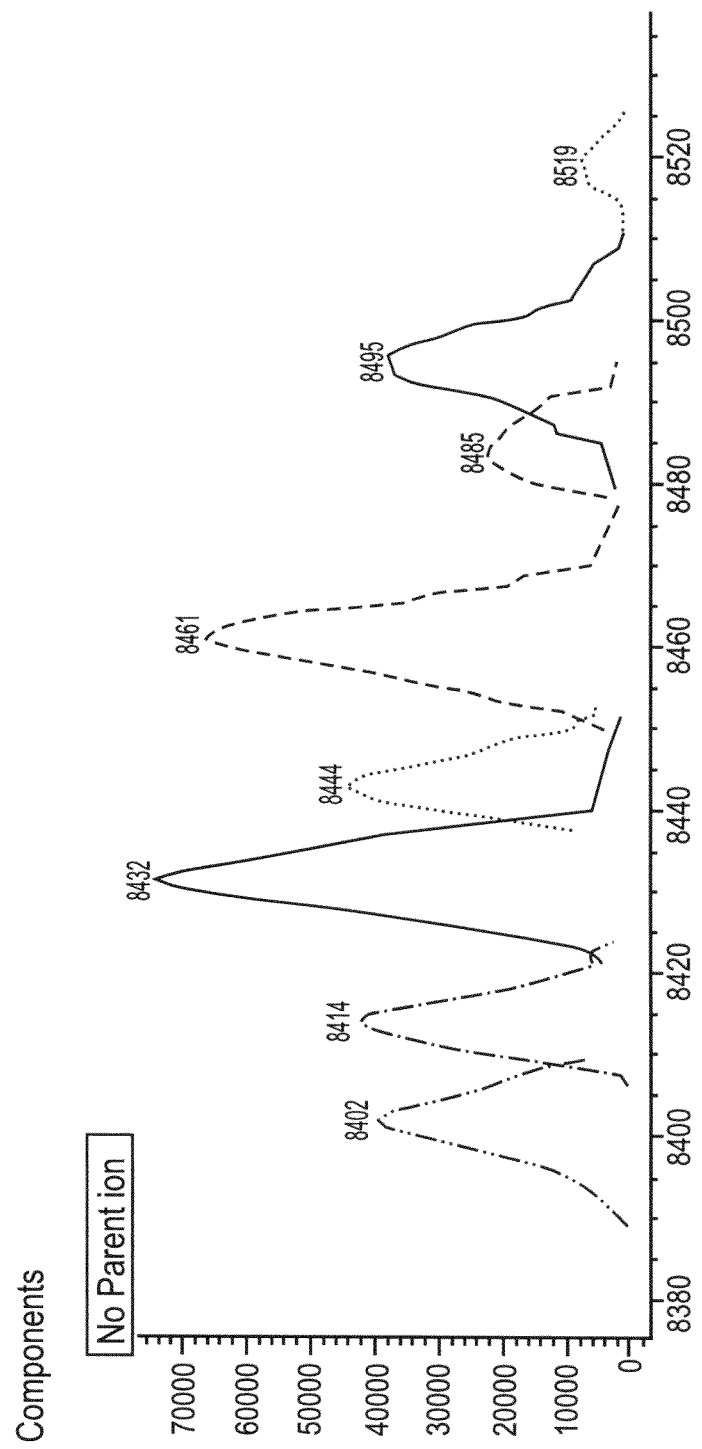
FIG. 9 illustrates mass spectrometry analysis of the synthetic RNA following a 24 hour incubation with formalin.
Figure 10:
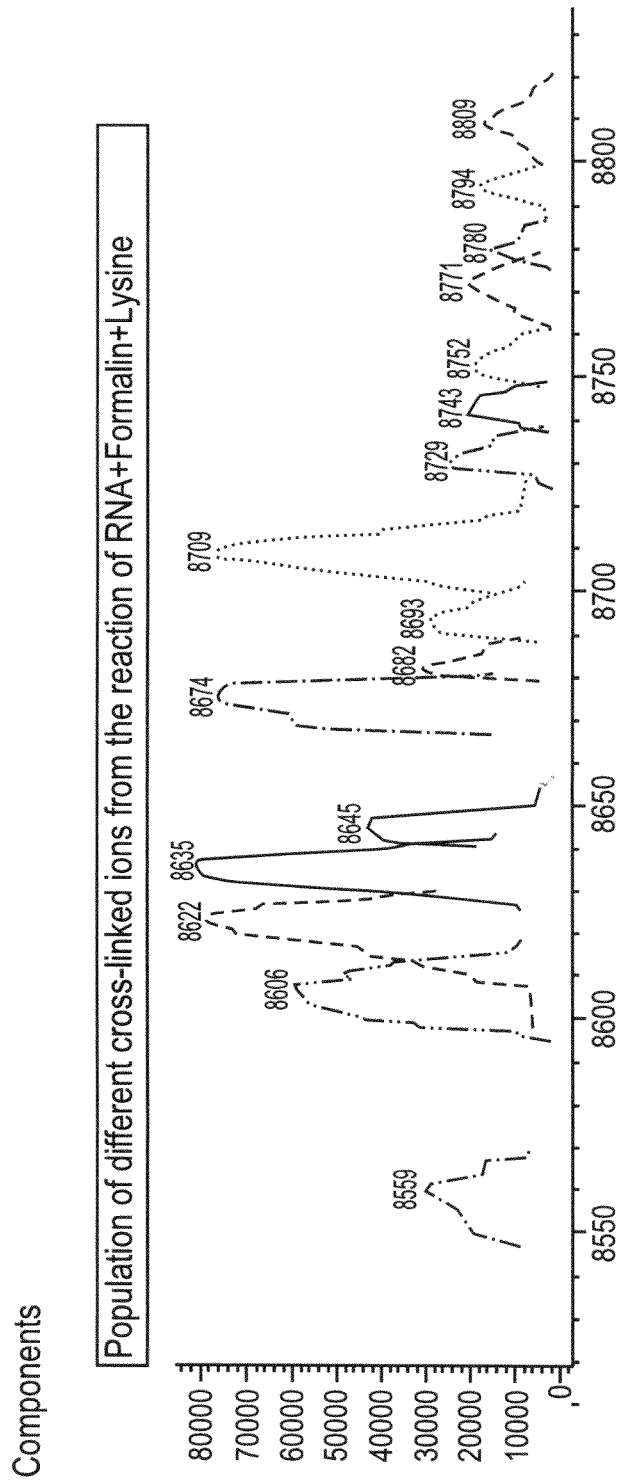
FIG. 10 illustrates mass spectrometry analysis of the synthetic RNA following a one hour incubation with formalin and lysine.
Figure 11:
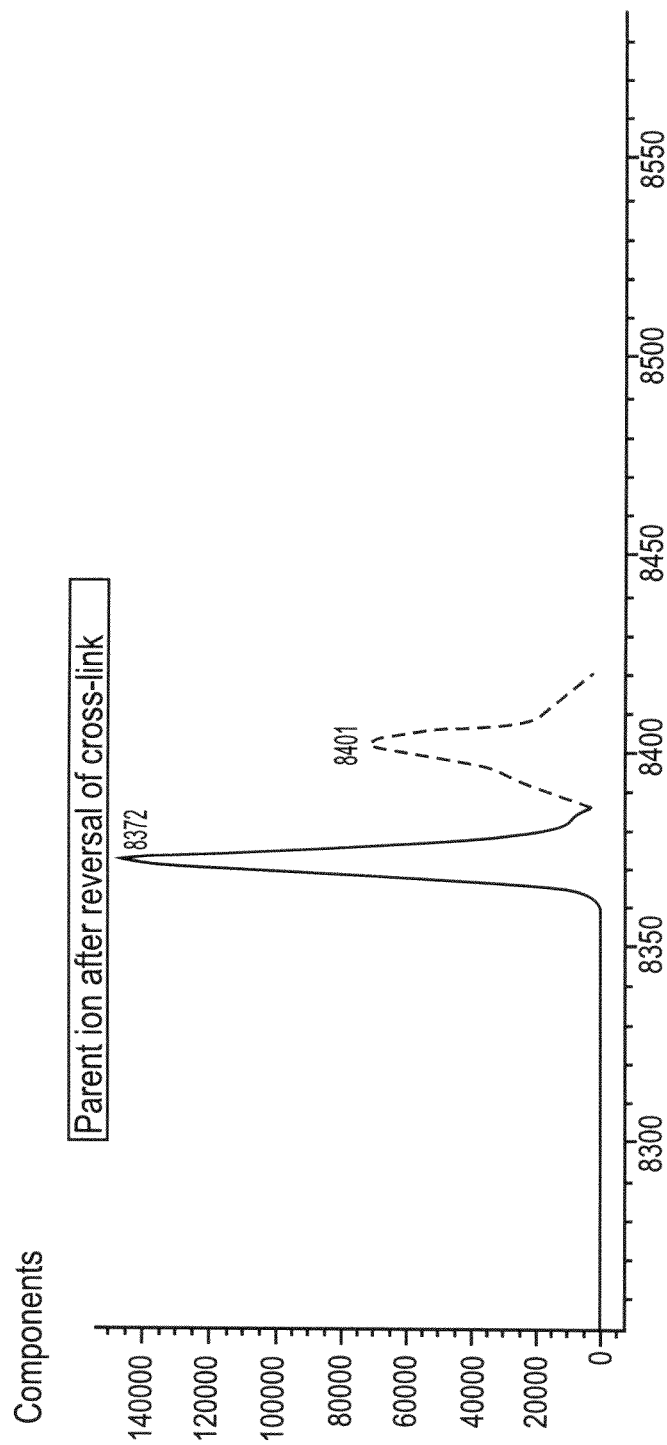
FIG. 11 illustrates mass spectrometry analysis of the synthetic RNA following a one hour incubation with formalin and lysine and subsequent release of cross-link chemistry with ethanoldiame (EDA). The figure shows that the starting RNA was regenerated from cross-linked RNA-lysine adducts.
Figure 12:
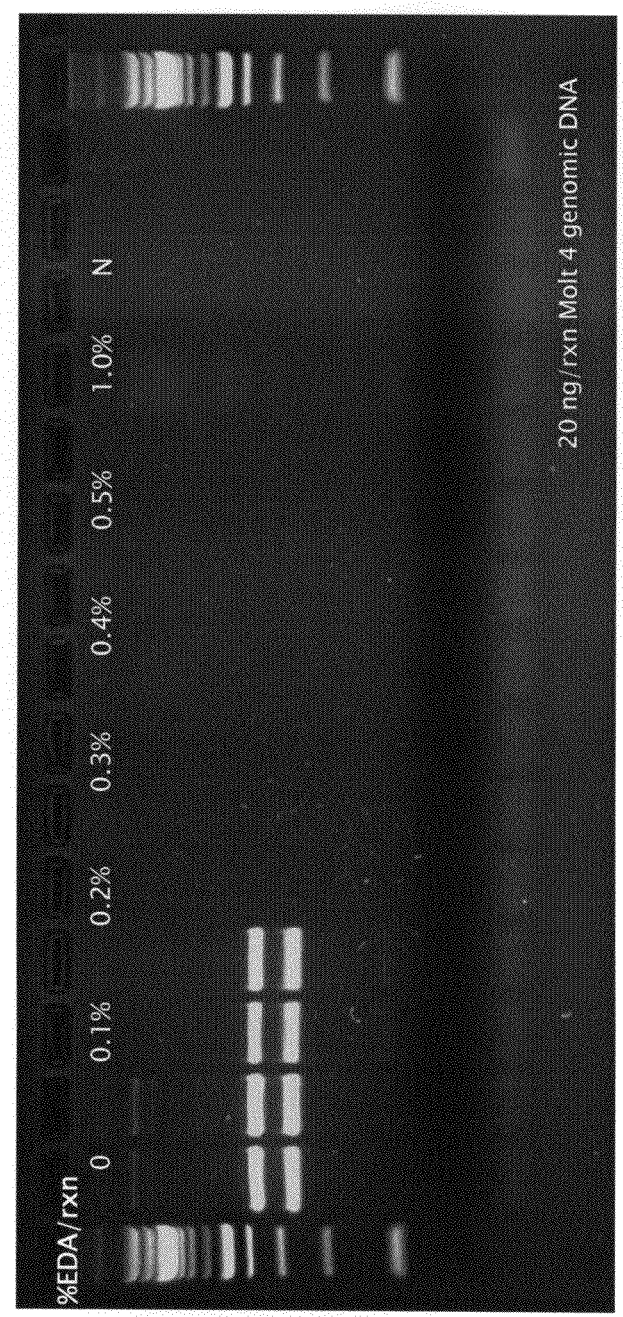
FIG. 12 illustrates the effect of ethanoldiamine (EDA). The concentration of EDA used is shown as a percentage. Notably, in this system, 0.2% (about 50 mM) and more EDA was found to inhibit the PCR reaction.
Figure 13:
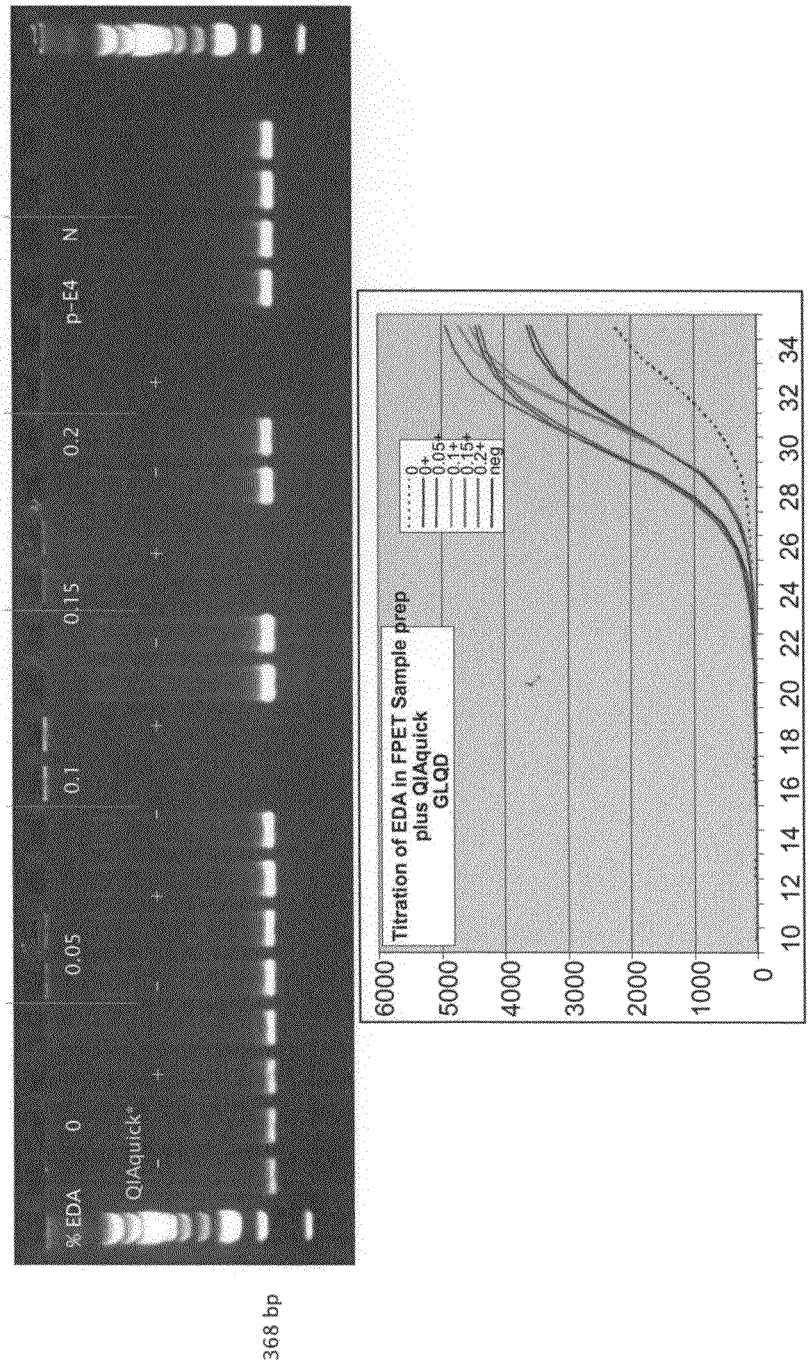
FIG. 13 illustrates the reversal of cross-linkage with EDA in a formalin fixed paraffin embedded tissue (FFPET) sample. The top portion of the figure shows that at lower concentrations of EDA, amplification occurs whether or not the QIAquick™ purification is performed. However, the quantity of amplification is lower compared to other lanes. At concentrations of EDA that inhibit amplification (e.g., greater than 0.1% (about 25 mM)) there is only amplification when the Qiaquick™ purification is performed, demonstrating an advantage to removing or otherwise inactivating the EDA prior to amplification. The portion of the figure provides a graph of cycle thresholds vs. signal and illustrates that an increasing amount of EDA, in combination with an EDA removal step, is effective in significantly improving the amount of DNA in the sample that is accessible for PCR amplification.
Figure 14:
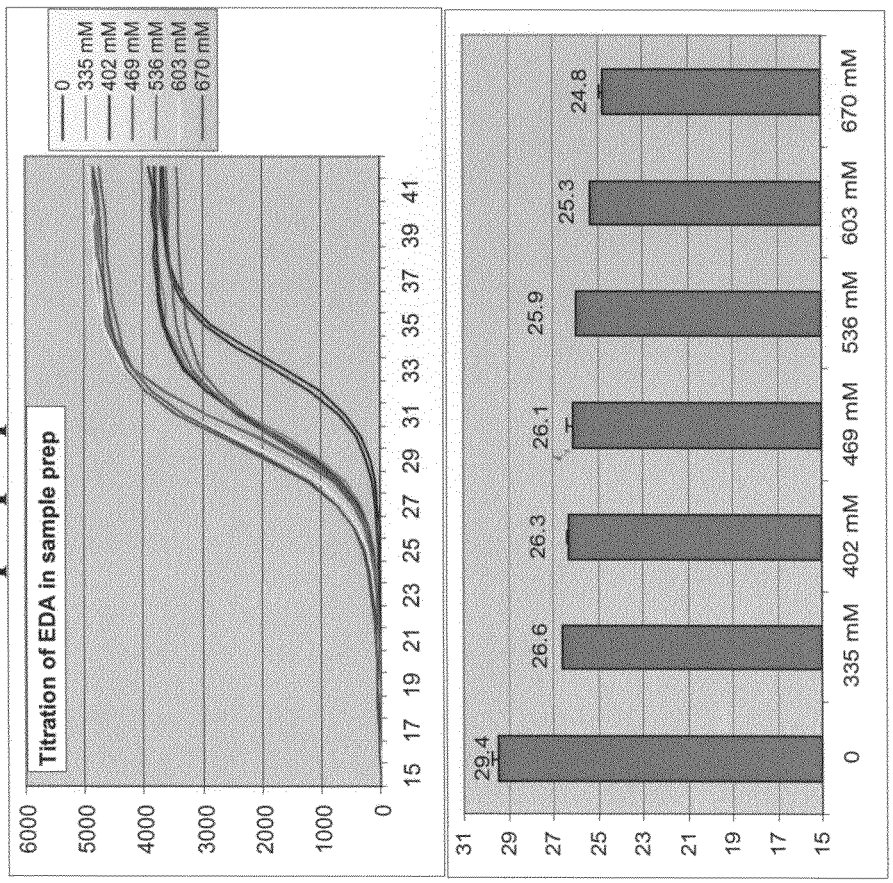
FIG. 14 also illustrates that treatment of FFPET samples with increasing amount of EDA in sample prep results in improved accessibility of nucleic acids for amplification. In the top portion of the figure, cycle threshold (x-axis) is graphed versus amplification signal. In the bottom portion, cycle threshold is in the y-axis and concentration of EDA is in the x-axis.

As shown in FIG. 1, formaldehyde results in the cross-linkage of nucleic acids to primary amines, notably amino acids such as lysine and arginine in proteins. As a result of the cross-linking, various biological components in formaldehyde-fixed samples are not accessible to modern detection methods. The present invention provides methods of reversing the cross-linking, thereby rendering more of the biological components accessible for detection.

Reversal of the cross-linking in formaldehyde-treated samples is achieved by contacting the samples with a sufficient amount of an alkyl amine to release the cross-linking reaction. An exemplary reversal of cross-linking is depicted in FIG. 1 (showing in this case nucleic acids cross-linked by formaldehyde to lysine, and the subsequent reversal of the reaction with an alkyl amine).

Once cross-linked samples are contacted with an alkyl amine, cross-linking of nucleic acids and proteins is reduced or eliminated, thereby allowing for improved detection of these components.

II. Methods for Rendering Cross-Linked Components More Accessible

The present invention provides for methods of rendering formaldehyde cross-linked components of a biological sample more accessible for detection by contacting the sample with an alkyl amine. The quantity of alkyl amine used to render the components more accessible can vary and will depend in part on the specific alkyl amine used, the component to be detected, and the detection method to be used as different detection methods have different sensitivities and so may require more or less of the component to be accessible.

Ideally, the amount of a component rendered accessible to a particular detection method will be the entire amount of the component in the sample. However, generally, the amount of component rendered accessible for detection will be less than the entire quantity of the component in the sample. In some embodiments of the invention, a sufficient amount of alkyl amine is used under conditions to render at least about two times the amount of the component accessible for detection as would be accessible (using the same detection method) if the sample was not treated with the alkyl amine. In some embodiments, a sufficient amount of alkyl amine is used under conditions to render at least about 5, 10, 20, 100 times the amount of the component accessible for detection as would be accessible (using the same detection method) if the sample was not treated with the alkyl amine. In some embodiments, the concentration of alkyl amine used to release the cross-linking of the sample is between about 0.01% and about 5% (or more), e.g., between about 0.01% and about 1%, between about 0.05% and about 2%, about 0.05% and about 1%, and about 0.1 and about 1%.

Those of ordinary skill in the art will appreciate that the conditions (e.g., time and temperature) in which the sample and alkyl amine are combined will affect the ability and amount of cross-linkage reversal. Alkyl amine treatment is effective at ambient (e.g., between 20-40 or 50° C.) temperature and thus does not necessarily require a heating step to release cross-linkages. This can be particularly useful when detecting components that are relatively labile, such as RNA. Nevertheless, higher temperature (e.g., 80-100° C., 90-100° C., 90-99° C., etc.) may further improve the accessibility of nucleic acids or proteins for detection.

Moreover, the amount of time the alkyl amine is incubated with the sample will affect the amount of the components rendered accessible for detection. For example, the samples can be incubated with the alkyl amine for at least about 5, 10, 20, 30, 60, 120 minutes or more. While a longer time of incubation may increase the amount of component that is released from cross-linking, this may need to be balanced with how labile a particular component may be. For example, it may be desirable to use a shorter incubation time when a labile component such as RNA is to be detected. On the other hand, a less labile component, such as protein or DNA, can be exposed to a longer incubation without harming the component.

It will be recognized that different alkyl amines can be used to release cross-linking. Without intending to limit the scope of the present invention, the selected alkyl amine will generally be capable of releasing the components from the formaldehyde-induced cross linkages and reverting the components (e.g., nucleic acids and/or protein) to substantially the same component as existed prior to the formaldehyde cross-linking. The cross-linking reaction is believed to be a reversible process that proceeds by reaction of formaldehyde and a first amine to form a hemiaminal, followed by dehydration to afford an imine. The imine reacts with a second amine to afford the product animal. The process reverts to the starting materials by reaction of the imine with water instead of a second amine. It is believe the alkyl amine of the present invention releases the components from the formaldehyde-induced cross linkages by acting as a competitive reactant in the formation of the imine and the animal. When the cross-linkages release as part of the equilibrium process, the imine intermediate and the formaldehyde react with the alkyl amine, thereby releasing the components from the formaldehyde-induced cross linkages. Generally, any alkyl amine with a primary amine (and sometime a secondary amine) will be effective. It will be appreciated that various substitutions to the alkyl amine are possible without substantially affecting the ability of the amine to reverse the cross-linking or creating other reactive moieties that would react with sample components, as long as such substitutions do not substantially interfere with the ability of the amine function to react. For example, ethanolamine is effective in reversing cross-linkages. Ethylenediamine is also effective, though it will be recognized that other diamines will similarly be effective in the methods of the invention. Further while shorter alkyl chains (e.g., having 1, 2, 3, 4, 5 carbons) can sometimes be preferable, longer carbon chains may also be used.

Any type of formaldehyde cross-linked biological sample can be used according to the methods of the invention. Generally, the tissue samples will be derived from animal tissues. In some embodiments, the samples will be embedded in paraffin. For example, the samples can be formalin fixed paraffin embedded tissue (FFPET). In some embodiments, the samples have been obtained from an animal (e.g., a human) and then stored in a formaldehyde-containing solution to stabilize the sample prior to analysis, thereby cross-linking the nucleic acids and/or protein in the sample. For example, a cervical or other gynecological swab (e.g., for detection of sexually transmitted disease) can be stored in a solution containing formaldehyde, thereby cross-linking the nucleic acids and/or protein in the sample. The cross-linking can be subsequently reversed using an alkyl amine according to the methods of the invention.

To further render the sample components accessible to detection, additional purification or other steps may be included in the methods of the invention. For example, if a nucleic acid component of the sample is to be detected, it can be helpful to treat the sample (e.g., before or following alkyl amine treatment) with a protease, or otherwise degrade the protein in the sample. An exemplary protease is proteinase K, though it will be appreciated that various other proteases could be substituted.

Also depending on the detection method to be used subsequently, it can be desirable to remove or at least reduce the amount of alkyl amine associated with the sample before detecting a component. For example, the inventors have found it helpful to purify the nucleic acids in the sample from other components of the sample as well as from the alkyl amine by using a reagent or device such as a spin column to purify nucleic acids from other parts of the sample. An exemplary device is a silica-based spin column with affinity for nucleic acids (such as the Qiaquick™ spin column from Qiagen, Valencia, Calif.), though of course other purification methods may also be used to remove the alkyl amine.

Alternatively, the amine can be chemically neutralized so as to no longer be capable of significant interference with detection of a particular component.

II. Detection of Components of Cross-Linked Biological Samples

Any detection method may be used in combination with the alkyl amine treatment described above to detect a component of the previously cross-linked sample. As described in further detail below, exemplary components of the sample for which cross-linking interferes with detection include nucleic acids and proteins. Detection of components can involve simply determining the presence or absence of a particular component or part (e.g., a particular protein or nucleic acid sequence) of the component. Alternatively, detection can involve quantification of the component and/or characterization of the component. Characterization can include, for instance, peptide or nucleic acid sequencing and/or determination of post-transcriptional or translational modifications, including, e.g., glycosylation, phosphorylation, etc.

A. Nucleic Acids

Numerous methods for detecting nucleic acids are known in the art. DNA or RNA (including mRNA, rRNA, etc.), or both can be detected. Detection can include quantification of a particular sequence or RNA, and/or characterization of a nucleic acid, for example, by nucleotide sequencing or sequence-specific hybridization techniques (e.g., such as those used to detect single nucleotide polymorphisms (SNPs) and the like).

As many paraffin-embedded, formaldehyde-treated samples are relatively small, it is often desirable to use amplification methods to amplify a particular nucleic acid to assist in detection of nucleic acids. Any type of amplification method may be used, including exponential amplification methods, linear amplifications, thermo cycling or isothermal methods, etc. Suitable amplification methods include, but are not limited to, the polymerase chain reaction (PCR) (*Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Current Protocols in Molecular Biology, Ausubel, 1994-1999, including supplemental updates through April 2004; Sambrook & Russell, *Molecular Cloning, A Laboratory Manual* (3rd Ed, 2001)), the ligase chain reaction (LCR) (U.S. Pat. Nos. 5,185,243, 5,679,524 and 5,573,907; EP 0 320 308 B1; WO 90/01069; WO 89/12696; and WO 89/09835), cycling probe technology (U.S. Pat. Nos. 5,011,769, 5,403,711, 5,660,988, and 4,876,187, and PCT published applications WO 95/05480, WO 95/1416, and WO 95/00667), Invader™ technology (U.S. Pat. Nos. 5,846,717; 5,614,402; 5,719,028; 5,541,311; and 5,843,669), Q-Beta replicase technology (U.S. Pat. No. 4,786,600), NASBA (U.S. Pat. No. 5,409,818; EP-0 329 822), TMA (U.S. Pat. Nos. 5,399,491, 5,888,779, 5,705,365, 5,710,029), SDA (U.S. Pat. Nos. 5,455,166 and 5,130,238). Numerous different polymerases can be used in the amplifications. A representative thermostable enzyme isolated from *Thermus aquaticus* (Taq) is described in U.S. Pat. No. 4,889,818 and a method for using it in conventional PCR is described in Saiki et al., 1988, *Science* 239:487-91. Another representative thermostable enzyme includes *Thermus* species Z05 DNA polymerase. See, e.g., U.S. Pat. No. 5,674,738. Optionally, real-time PCR or other quantitative amplification techniques can be used to quantify a particular nucleic acid sequence. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1): 106-10, 112-5 (2003); Deiman B, et al., *Mol. Biotechnol.* 20(2):163-79 (2002). This can be particularly useful following reverse transcription reactions (RT-PCR) so that RNA levels for one or more gene can be measured within a sample. RT-PCR methods are well known to those of skill (see, e.g., *Current Protocols in Molecular Biology* (Ausubel et al., eds., 2002)) and are readily adapted for quantitative amplification methods.

Other methods can also be used to detect nucleic acids. For example, nucleic acids can be isolated from a sample and hybridized to a probe. In some instances, the probe will be linked to a solid support (e.g., a microarray).

B. Proteins

Protein components of a sample can also be detected following treatment with an alkyl amine. Any of a variety of protein detection and characterization methods may be employed according to the method of the present invention.

An exemplary protein detection method is mass spectrometry. Exemplary mass spectrometry methods include, but are not limited to, electrospray ionization and matrix-assisted laser desorption/ionization (MALDI), including MALDI time of flight (MALDI-TOF) methods. See, e.g., Karas, M.; Hillencamp, F. Anal. Chem. 60:2301 1988); Beavis, R. C. Org. Mass Spec. 27:653 (1992); Creel, H. S. *Trends Poly. Sci.* 1(11):336 (1993).

One alternative to detection with mass spectrometry is use of electrophoresis to separate and subsequently detect proteins of interest. Electrophoresis methods include two-dimensional electrophoresis methods. The methods can optionally include subsequent western blot detection of proteins with antibodies.

Other options include immuno-detection of proteins. Various ELISA and other formats for immuno-detection of proteins are well known.

III. Kits

The present invention also provides kits useful for employing the above-described methods of the invention. As such, the kits can comprise one or more of the reagents described herein. Optionally, the kits can include written (paper) or electronic instructions for their use.

In some embodiments, the kits of the invention will include an alkyl amine with at least one additional reagent for detection or improving detection of a nucleic acid or protein. For example, in some embodiments, the kits comprise an alkyl amine and a protease (including but not limited to proteinase K) for degrading protein and rendering nucleic acids even more accessible to detection. Other reagents for detection or improving detection of a nucleic acid or protein include, e.g., reagents useful for amplifications. For example, a typical polymerase chain reaction can include, without limitation, as reagents upstream and downstream primers, at least one template, deoxyribonucleoside triphosphates (including dATP, dCTP, dGTP, TTP, dUTP), a polymerase enzyme, buffers, metal cations and salts. A kit for an RT-PCR reaction can also include a reverse transcriptase and/or primers. For quantitative (e.g., "real-time") amplification, one or more polynucleotide probes are employed to hybridize to the desired target. The probes are typically labeled with a detectable label, e.g., a fluorescent label. An exemplary probe is a Taqman™ probe, though it will be appreciated that other types of probes can be used to monitor a target in a quantitative amplification reaction. A nucleic acid sequence-based amplification (NASBA) reaction can include primers, reverse transcriptase, RNase H, and a DNA polymerase. A transcription-mediated amplification (TMA) reaction can include primers, reverse transcriptase, and an RNA polymerase. An strand displacement amplification (SDA) reaction can include a modified nucleotide and a restriction endonuclease. Certain amplification reactions can also include deoxyUridine N-Glycosylase (UNG) as an ancillary amplification reagent (e.g., Amperase®, Roche Molecular Sciences, Alameda, Calif.) (see, Kleiboeker, *Virol J* (2005) 11:29).

Other reagents for detection or improving detection of a nucleic acid or protein include, e.g., reagents or devices for purifying proteins or nucleic acids, for example as described herein.

IV. Reaction Mixtures

The present invention also provides reaction mixtures. An exemplary reaction mixture will comprise a formaldehyde-fixed sample, optionally including paraffin, and an alkyl amine as described herein. The reaction mixtures can include the concentrations of alkyl amine that are described above. Further, the reaction mixtures are optionally at the temperatures recited above. Reaction mixtures can optionally further include a protease (e.g., proteinase K).

EXAMPLE

Example 1

This example illustrates reversal of cross-linking chemistry of nucleic acids with alkyl amines.

A synthetic oligonucleotide (DNA sequence: AAG TCA GAA GGE AAA (SEQ ID NO:1) [E=5-methyl-dC]; 3 µM) or RNA sequence: FCCCUCGCAGCCGUCCAAC-CAACUCA (SEQ ID NO:2) [F=Fluorescein]; 3 µM) was treated with formalin (buffered formalin solution, 10%, Sigma-Aldrich, HT50-1-1) in the presence of lysine (0.3 M) and incubated at 4° C. for 24 hours. The kinetics of the cross-linking chemistry was monitored by LC-MS analysis. The MS data suggests that the products in the reaction mixture consist of oligonucleotides cross-linked with lysine via a methylene bridge and also oligonucleotide-formaline adducts. After 24 hours, all oligonucleotides detected appeared to be cross-linked in the reaction mixture. The excess formalin and lysine were separated from the reaction mixture prior to the ethylenediamine treatment. To this reaction mixture (400 µl) was added ethylenediamine (100 µl, 2.0 M) and incubated at room temperature for 1.0 hour. The LC-MS analysis of the sample confirms quantitative reversal of cross-linking chemistry regenerating starting oligonucleotide from all cross-linked adducts. Results of LC-MS analysis at various steps in this procedure are illustrated in FIGS. 2-5.

A further example of cross-linkage reversal is illustrated in FIGS. 6-11, this time using a synthetic RNA molecule as an example.

Example 2

An exemplary protocol for Detection of DNA is provided below:

Step 1: Tissue Sectioning

Cut a 20µ tissue section using Microtom RM2255 and place section in a 1.5 mL Eppendorf or screw cap tube.

Step 2: Lysis Reagent

Add EDA to Lysis Reagent for a final concentration of 500 mM/225 µL. Add 200 µL Lysis Reagent/EDA to each tube containing specimen.

Step 3: Heat Step

Incubate each specimen for 30 minutes in a heat block set at 98° C. After the first five minutes, remove each specimen from the heat block and vortex briefly. After vortexing, centrifuge at 20,817 rcf (eg. Eppendorf 5417C, 14,000 rpm) for 5 seconds to bring all paraffin and tissue into solution. Ensure there is no paraffin or tissue left on the sides of the tube. Return to heat block for remaining 25 minutes.

After 25 minutes, remove the specimen from the heat block and centrifuge at 20,817 rcf (eg. Eppendorf 5417C, 14,000 rpm) for 5 seconds to bring all paraffin and tissue into solution. Cool each specimen for 5 minutes at room temperature.

Step 4: Lysis+Proteinase K Steps

Add 20 µL of PK to each tube containing specimen. Vortex briefly, then centrifuge at 20,817 rcf (eg. Eppendorf 5417C, 14,000 rpm) for 5 seconds to bring all the paraffin and tissue into solution. Ensure there is no paraffin or tissue left on the sides of the tube.

Incubate each specimen for 1 hour in a heat block set at 65° C. Vortex briefly, then centrifuge at 20,817 rcf (eg. Eppendorf 5417C, 14,000 rpm) for 5 seconds bring all the paraffin and tissue left on the sides of the tube.

Step 5: Proteinase K Inactivation Step

Incubate each lysed specimen in a heat block set at 98° C. for 10 minutes.

After the 10 minutes incubation period, quickly remove each specimen from the heat block set at 98° C. and centrifuge for 20 minutes at 20,817 rcf (eg. Eppendorf 5417C, 14,000 rpm) to remove debris from the lysate. If the lysate is allowed to cool excessively prior to centrifugation, a paraffin solidified top layer will not form and the paraffin will be removed along with the lysate. Preferably, the paraffin forms a solidified top layer.

Step 6: Centrifugation Steps to Remove Debris

Label one new 1.5 mL screw-cap tube for each specimen with appropriate sample identification.

Transfer the lysate to the newly labeled 1.5 mL tube. Avoid the paraffin top layer and cell debris in the pellet found at the bottom of the tube.

If sample needs further clearing, centrifuge the lysate for an additional 15 minutes 20,817 rcf (eg. Eppendorf 5417C, 14,000 rpm). Transfer the lysate to a new labeled 1.5 mL tube.

Pre-PCR Lysate Clean-Up

Transfer 100 µL lysate to a new, labeled 1.5 mL tube. Process according to the QIAquick® PCR Purification Kit (QIAGEN Sciences). Elute sample with final volume of 100 µL.

Example 2

This example illustrates reversal of cross-linking chemistry of protein-protein with ethylenediamine.

Figure 15:
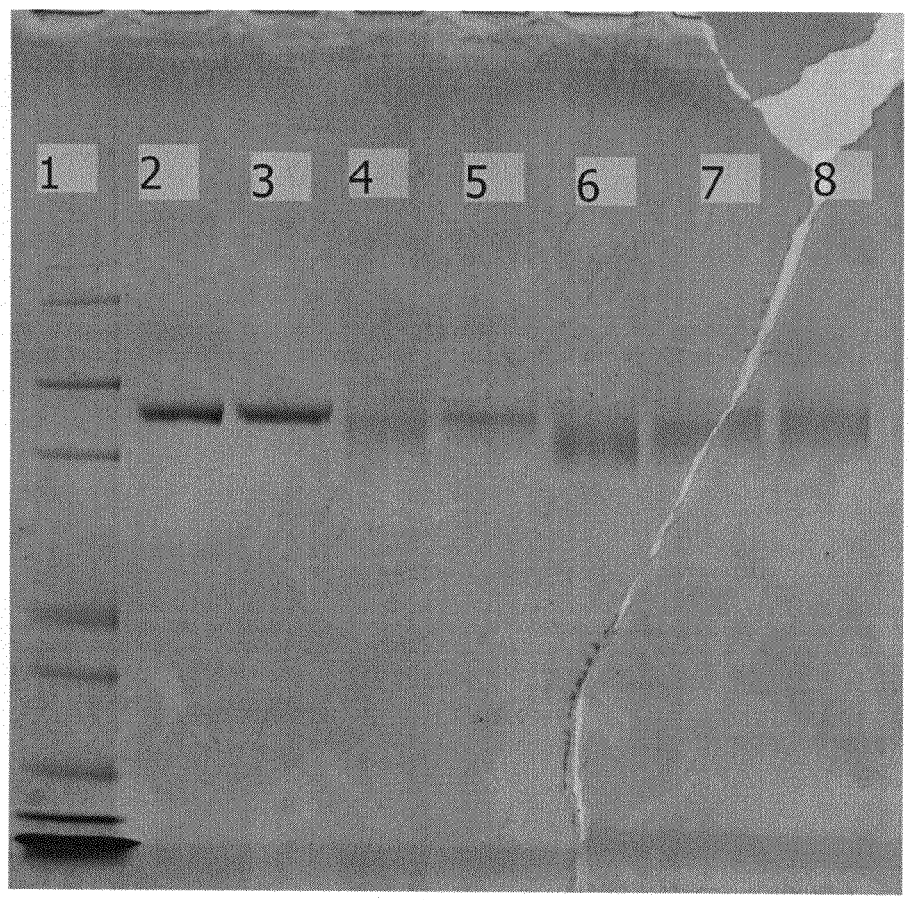
FIG. 15 illustrates an SDS-PAGE gel and shows the results of formalin-cross-linking of bovine serum albumin (BSA) and subsequent reversal of the cross-linking by treatment with EDA.

A bovine serum albumin (BSA) protein (100 µg, 10 µg/µl) was added to a formalin solution (65 µl, buffered formalin solution, 10%, Sigma-Aldrich, HT50-1-1) and incubated at 4° C. Aliquots of the sample were taken after 14 hours and 36 hours (25 µl at each time point). Ethylenediamine (25 µl, 2.0 M) was then added to these aliquots and they were incubated at room temperature for 1 hour. The samples were then analyzed by SDS gel (FIG. 15). As shown in lane 4 (incubation of protein in formalin at 4° C. for 14 hours) of FIG. 15, protein-protein cross-linking was complete. Lane 5 (incubation of protein-protein cross-linked product with ethylenediamine at room temperature for 1 hour) of FIG. 15 indicated that the protein-protein cross-linking chemistry is reversible in the presence of ethylenediamine. However, if the cross-linking time in formalin is extended, the cross-linking is incompletely reversed (lanes 6-8 of FIG. 15).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for detecting one or more components of a formaldehyde cross-linked biological sample, the method comprising
contacting the sample with a sufficient amount of an alkyl amine to release at least a portion of the cross-linked component, wherein the alkyl amine is selected from the group consisting of ethylenediamine, and propylamine, thereby improving the accessibility of the one or more components for analysis; and
detecting the component.

2. The method of claim 1, wherein the component is a nucleic acid.

3. The method of claim 1, wherein the component is a protein.

4. The method of claim 1, wherein the alkyl amine is ethylenediamine.

5. The method of claim 1, wherein the alkyl amine is propylamine.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: synthetic oligonucleotide DNA sequence
<220> FEATURE:
<221> NAME/KEY: modified_base
<222> LOCATION: (12)..(12)
<223> OTHER INFORMATION: n = m5c

<400> SEQUENCE: 1
aagtcagaag gnaaa                                                     15

<210> SEQ ID NO 2
<211> LENGTH: 25
<212> TYPE: RNA
<213> ORGANISM: Artificial Sequence
<220> FEATURE:
<223> OTHER INFORMATION: synthetic oligonucleotide RNA sequence
<220> FEATURE:
<221> NAME/KEY: modified_base
<222> LOCATION: (1)..(1)
<223> OTHER INFORMATION: c modified by fluorescein (F)

<400> SEQUENCE: 2
cccucgcagc cguccaacca acuca                                          25
```